United States Patent [19]

Smith

[11] Patent Number: 4,534,050
[45] Date of Patent: Aug. 6, 1985

[54] X-RAY GONIOMETER

[75] Inventor: Howard W. Smith, Lawrence, Kans.

[73] Assignee: The United States of America as represented by the Secretary of the Air Force, Washington, D.C.

[21] Appl. No.: 448,162

[22] Filed: Dec. 9, 1982

[51] Int. Cl.³ .................. A61G 13/00; A61B 17/00
[52] U.S. Cl. .................................. 378/81; 378/79; 128/303 B; 269/328
[58] Field of Search .......... 378/79, 80, 81, 208, 378/209, 210; 269/328; 128/92 A, 92 E, 92 R, 303 B

[56] References Cited

U.S. PATENT DOCUMENTS

| | | | |
|---|---|---|---|
| 2,035,952 | 3/1936 | Ettinger | 128/92 A |
| 2,508,449 | 5/1950 | Davis, Jr. et al. | 250/57 |
| 2,568,191 | 9/1951 | Grimm | 311/10 |
| 3,262,452 | 7/1966 | Hardy et al. | 128/303 |
| 3,384,086 | 1/1966 | Rocha-Miranda | 128/303 B |
| 3,466,439 | 9/1969 | Setala | 250/54 |
| 3,655,178 | 4/1972 | Vezina | 269/323 |
| 3,859,982 | 1/1975 | Dove | 378/208 |
| 4,360,028 | 11/1982 | Barbier | 128/303 B |

Primary Examiner—Craig E. Church
Assistant Examiner—Charles Wieland
Attorney, Agent, or Firm—Donald J. Singer; Bobby D. Scearce

[57] ABSTRACT

An X-ray goniometer is provided which comprises, a pair of wooden endplates held in a parallel, adjustably spaced relationship by a plurality of connecting dowel rods, a rotatable support mounted to each endplate, each support being rotatable about a common axis perpendicular to the endplates, for supporting each end of the specimen, and means to position the supports in any given angular orientation about the axis. Means may be included to adjust the spacing between endplates and between each support and the axis.

7 Claims, 3 Drawing Figures

U.S. Patent   Aug. 6, 1985   4,534,050
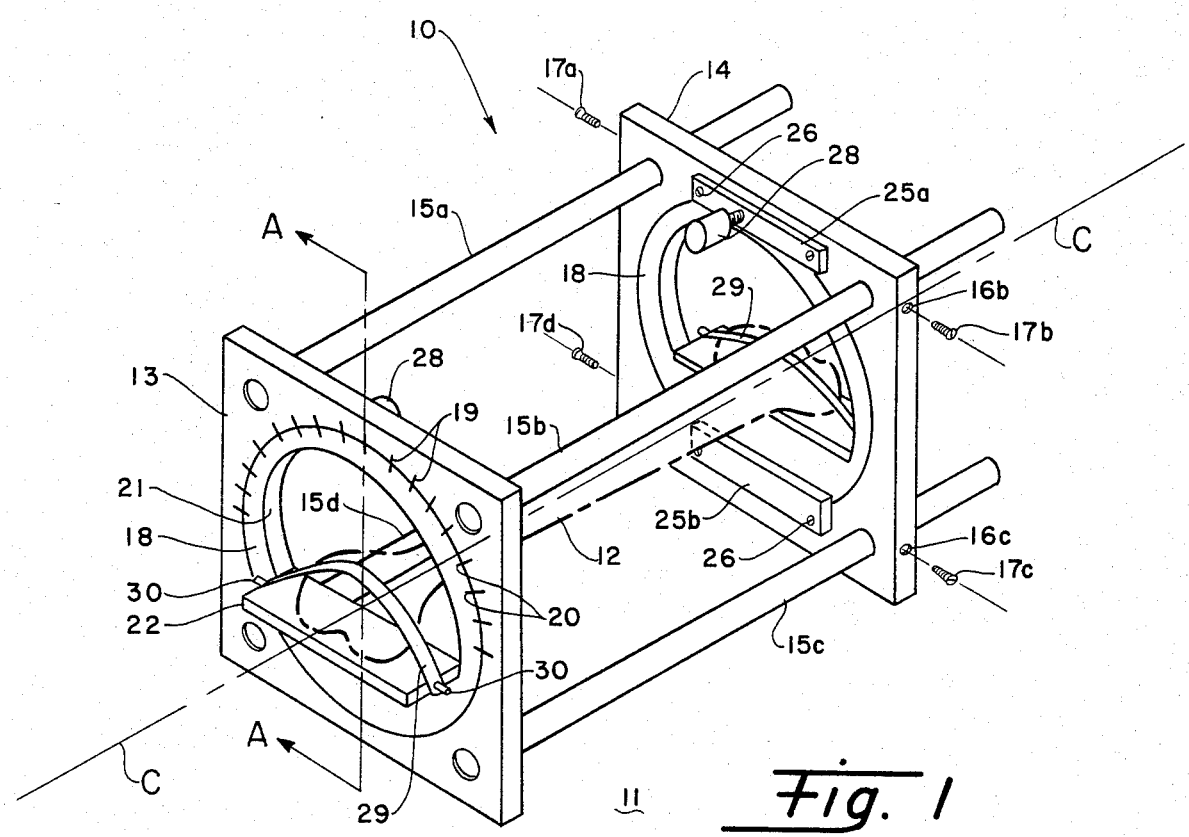
*Fig. 1*
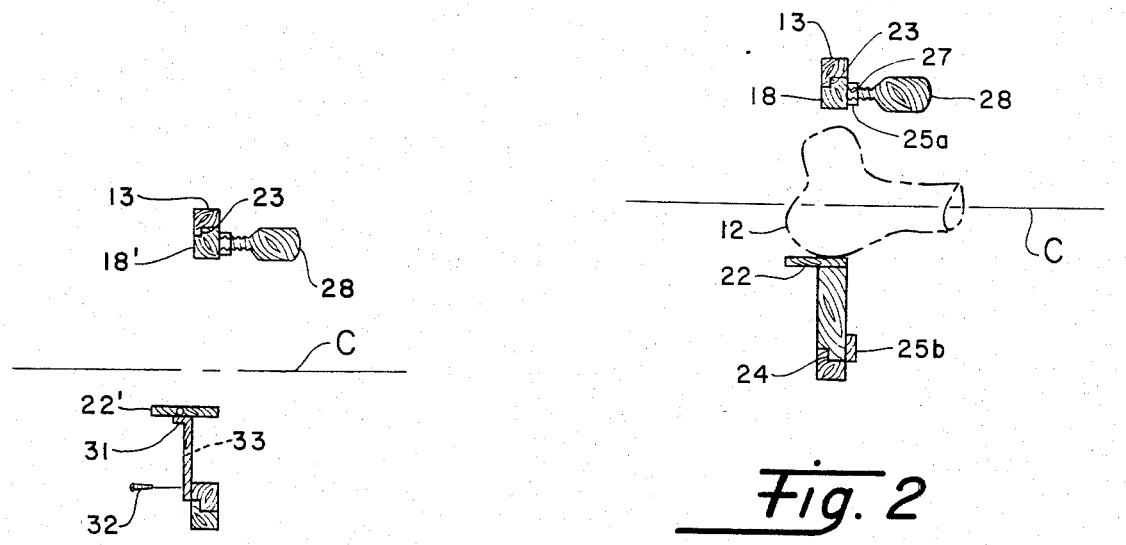
*Fig. 2*
*Fig. 3*

X-RAY GONIOMETER

RIGHTS OF THE GOVERNMENT

The invention described herein may be manufactured and used by or for the Government of the United States for all governmental purposes without the payment of any royalty.

BACKGROUND OF THE INVENTION

This invention relates generally to the field of devices for supporting a specimen for X-ray examination, and more particularly to a device for supporting a specimen in a preselected orientation for X-ray filming purposes.

In the examination of specimens by X-ray, it is a common and desirable practice to obtain views of the specimen taken at a variety of orientations. The present invention provides a device for holding a specimen in a desired angular orientation about its axis. A principal utility of the invention may be found in the X-ray analysis of specimens comprising whole bones, to position the specimens in a preselected orientation during exposure to X-rays, as part of studies of the mechanical properties and fracture patterns of whole bones.

It is therefore an object of the present invention to provide a device for accurately positioning a specimen relative to X-ray equipment for the purpose of obtaining X-ray photographs of the specimen.

It is a further object of the present invention to provide a device for positioning the specimen at any desirable angular orientation relative to a preselected reference position for the purpose of obtaining X-ray photographs.

These and other objects of the present invention will become apparent as the detailed description of certain representative embodiments thereof proceeds.

SUMMARY OF THE INVENTION

In accordance with the foregoing principles and objects of the present invention, an X-ray goniometer is provided which comprises, a pair of wooden endplates held in a parallel, adjustably spaced relationship by a plurality of connecting dowel rods, a rotatable support mounted to each endplate, each support being rotatable about a common axis perpendicular to the endplates, for supporting each end of the specimen, and means to position the supports in any given angular orientation about the axis. Means may be included to adjust the spacing between endplates and between each support and the axis.

DESCRIPTION OF THE DRAWINGS

The present invention will be more clearly understood from the following detailed description of specific representative embodiments thereof read in conjunction with the accompanying drawings wherein:

FIG. 1 is an isometric view of a representative device of the present invention;

FIG. 2 is a view taken along line A—A of FIG. 1; and

FIG. 3 is an alternative configuration to that suggested in FIG. 2 showing an adjustable support.

DETAILED DESCRIPTION

Referring now to FIG. 1, presented therein is an isometric view of a representative goniometer 10 of the present invention. Goniometer 10 is configured to rest squarely upon the surface of an X-ray stage 11 of an X-ray machine, to support thereon for X-ray filming a specimen, such as that shown in phantom in FIG. 1 as bone specimen 12, and to hold specimen 12 in a desired orientation during exposure to X-rays. The embodiment depicted in FIG. 1 comprises a pair of substantially identical upright endplate assemblies 13, 14 configured to be held in a parallel spaced relationship by four horizontally disposed connecting rods 15a–d. For the device 10 shown, each endplate 13, 14 was fabricated of wood and had an overall size approximately 8½ inches square by about ½ inch thick, and rods 15a–d comprised ½-inch diameter solid wood dowel rods approximately 18 inches long. It is understood that the dimensions and materials of construction stated herein as comprising the various component parts of goniometer 10 shall not be limiting of the invention herein, as the invention may assume a wide range of shapes and sizes within the scope of these teachings, and may comprise a wide range of materials, such as plastic, wood, and the like, which do not substantially absorb, aberrate or otherwise interfere with the X-rays to which the specimen 12 is exposed.

Each rod 15a–d is joined to one of the endplates 13, at the respective corners thereof substantially as shown in FIG. 1. In the assembly of rods 15a–d to endplate 13, holes of appropriate size may be drilled into the corners of endplate 13 and rods 15a–d fixed therein by means such as glue, plastic pins or screws, or other means which results in a joint substantially transparent to X-ray.

Endplate 14 has near each corner thereof a hole of appropriate size, and in registering alignment with the respective holes in endplate 13, for slideably receiving a rod 15. By this configuration, endplate 14 may be positioned along rods 15a–d in any desired parallel spaced relationship to endplate 13 limited only by the length of rods 15a–d selected for use in goniometer 10. Means may be provided with endplate 14 to enable a user of goniometer 10 to selectively position endplate 14 at any desired position along rods 15 and lock endplate 14 in that position. For example, tapped holes 16a–d may be provided near each corner of endplate 14 adjacent the respective rods 15a–d for receiving set screws 17a–d, respectively, of wood, plastic, or the like. By this arrangement, specimens 12 of various lengths may be accommodated.

Each endplate 13, 14 has mounted thereto a rotatable support for supporting specimen 12, and, for this purpose for the embodiment depicted in FIG. 1, each endplate 13, 14 may have a central circular opening for receiving a rotatable circular shaped indexing member 18. Each rotatable member 18 is configured to be positionable at any desired angular position about an axis C substantially perpendicular to endplates 13, 14. A set of indexing marks 19 may be provided on the face of each endplate 13, 14 adjacent the respective openings therein, and a set of corresponding indexing marks 20 may be provided on the periphery of each member 18 by which the angular position of each member 18 within its respective opening may be gaged. Each member 18 may define a central opening 21 and may include a platform 22 spanning opening 21 for receiving and supporting a specimen 12.

Referring now to FIG. 2, shown therein is a sectional view of goniometer 10 taken substantially along line A—A of FIG. 1. As shown therein, a representative configuration for rotatably holding member 18 within the opening defined in endplate 13 may include an annular shoulder 23 on the wall defining the opening in the endplate 13, against which an abutting annular shoulder 24 on the periphery of member 18 may slide. Member 18 may then be rotatably held in place by a pair of wood retaining plates 25a, 25b secured to endplates 13, 14 by plastic screws 26 (see FIG. 1). Each retaining plate 25a may include a tapped hole 27 for receiving a set screw 28 configured to tighten against a surface of member 18 to provide means to hold member 18 in any desired angular position.

In order to secure specimen 12 to platforms 22 at any angular position of member 18, a clamping means may be included, which, in the FIG. 1 embodiment presented, may be represented by elastic straps 29 releasably attachable at each end to pegs 30 included at each end of platforms 22, substantially as shown. It is understood that many various clamping means may be used in conjunction with the specimen 12 support represented by platforms 22 as would occur to one with skill in the appropriate field, and the clamping means shown is intended to be representative only and not limiting of the invention herein.

Referring now to FIG. 3, it is seen that means may be included with goniometer 10 whereby the spacing between platforms 22 and axis C may be adjustable. A representative configuration may include a wooden bracket 31 supporting platform 22' and adjustably secured to member 18' by a plastic set screw 32 riding in slot 33 in one leg of bracket 31.

There is, therefore, provided by the invention herein a device for supporting a specimen at preselected angular positions relative to an X-ray apparatus. It is understood that certain modifications to the invention as described may be made, as might occur to one with skill in the field of this invention, within the scope of the appended claims. Therefore, all embodiments contemplated hereunder have not been shown in complete detail. Other embodiments may be developed without departing from the spirit of this invention or from the scope of the appended claims.

I claim:

1. A goniometer device for supporting a specimen on an X-ray apparatus during X-ray filming, which comprises:
   a. first and second upright endplates;
   b. a plurality of connecting rods and means for connecting said rods at respective ends thereof to said endplates for holding said endplates in a spaced parallel relationship on said X-ray apparatus;
   c. a first support, rotatably mounted to said first endplate, said first support and first endplate defining a first opening therethrough, for receiving and supporting a first end of said specimen, and a second support, rotatably mounted to said second endplate, said second support and second endplate defining a second opening therethrough, for receiving and supporting a second end of said specimen, said supports being rotatable about a common axis substantially perpendicular to said endplates; and
   d. a set of reference marks on each said endplate and said rotatable support for gaping the angular position of said supports about said axis relative to said endplates.

2. The device as recited in claim 1 wherein said connecting rods are substantially rigidly attached to said first endplate and slideably mounted to said second endplate whereby the spacing between said endplates may be adjusted.

3. The device as recited in claim 2 further comprising means on said second endplate and adjacent said connecting rods for locking said second endplate in a preselected position along said connecting rods relative to said first endplate.

4. The device as recited in claim 1 further comprising first and second clamping means on, respectively, said first and second supports, for releaseably attaching said specimen to said supports.

5. The device as recited in claim 4 wherein each of said endplates, connecting rods, connecting means, first and second supports, locking means, and first and second clamping means consist of a material substantially transparent to X-ray.

6. The device as recited in claim 1 wherein said first and second supports include first and second platforms and further comprises means connected to said platforms for adjustably positioning said platforms along a direction perpendicular to said axis, said supports and positioning means consisting of a material substantially transparent to X-ray.

7. The device as recited in claim 1 further comprising X-ray transparent means on each of said endplates for releaseably clamping each of said supports in a preselected angular position relative to said endplates about said axis.

* * * * *